(12) United States Patent
Karason

(10) Patent No.: US 6,936,073 B2
(45) Date of Patent: Aug. 30, 2005

(54) ARTIFICIAL LIMB SOCKET CONTAINING VOLUME CONTROL PAD

(75) Inventor: Gudjon G. Karason, Kopavogur (IS)

(73) Assignee: Ossur HF, Reykjavik (IS)

( * ) Notice: Subject to any disclaimer, the term of this patent is extended or adjusted under 35 U.S.C. 154(b) by 240 days.

(21) Appl. No.: 09/969,575

(22) Filed: Oct. 4, 2001

(65) Prior Publication Data

US 2002/0040248 A1 Apr. 4, 2002

Related U.S. Application Data

(60) Provisional application No. 60/237,381, filed on Oct. 4, 2000.

(51) Int. Cl.⁷ .................................................. A61F 2/80
(52) U.S. Cl. ...................................................... 623/37
(58) Field of Search .............................. 623/37, 36, 33, 623/27, 8, 56; 602/5

(56) References Cited

U.S. PATENT DOCUMENTS

| | | | |
|---|---|---|---|
| 1,319,637 A | 10/1919 | Blevens | |
| 3,520,002 A | 7/1970 | Wellington | 3/19 |
| 3,548,420 A | 12/1970 | Spence | |
| 3,663,973 A | 5/1972 | Spence | 5/348 |
| 3,889,301 A | 6/1975 | Bonner | |
| 4,300,245 A | 11/1981 | Saunders | 3/18 |
| 4,502,234 A | 3/1985 | Schaefer | 36/28 |
| 4,635,626 A | 1/1987 | Lerman | 128/165 |
| 4,654,038 A * | 3/1987 | Sakurai | 604/368 |
| 4,655,779 A | 4/1987 | Janowiak | 623/37 |
| 4,676,784 A * | 6/1987 | Erdman et al. | 604/368 |
| 4,681,577 A * | 7/1987 | Stern et al. | 604/378 |
| 4,685,914 A * | 8/1987 | Holtman | 604/368 |
| 4,758,466 A * | 7/1988 | Dabi et al. | 442/338 |
| 4,923,475 A | 5/1990 | Gosthnian | 623/37 |
| 5,087,513 A * | 2/1992 | Kim | 442/118 |
| 5,108,456 A | 4/1992 | Coonan | 623/37 |
| 5,133,776 A | 7/1992 | Crowder | 623/37 |
| 5,171,269 A | 12/1992 | Bark | |
| 5,246,464 A | 9/1993 | Sabolich | 623/33 |
| 5,314,496 A | 5/1994 | Harris | 623/31 |
| 5,314,497 A | 5/1994 | Fay | 623/34 |
| 5,328,935 A * | 7/1994 | Van Phan et al. | 521/64 |
| 5,387,245 A | 2/1995 | Fay et al. | 623/37 |
| 5,405,405 A | 4/1995 | Love | 623/37 |
| 5,409,771 A | 4/1995 | Dahmen | 428/327 |
| 5,425,762 A * | 6/1995 | Muller | 623/11.11 |
| 5,464,443 A | 11/1995 | Wilson | 623/37 |
| 5,480,430 A | 1/1996 | Carlisle et al. | 623/8 |
| 5,490,847 A * | 2/1996 | Correa et al. | 604/387 |
| 5,506,035 A * | 4/1996 | Van Phan et al. | 428/196 |
| 5,506,277 A * | 4/1996 | Griesbach, III | 521/84.1 |
| 5,507,836 A | 4/1996 | Pohlig | 623/37 |
| 5,549,709 A | 8/1996 | Caspers | 623/24 |
| 5,569,710 A * | 10/1996 | LaFleur et al. | 525/57 |
| 5,724,714 A | 3/1998 | Love | 29/458 |
| 5,728,170 A | 3/1998 | Becker et al. | |
| 5,735,906 A | 4/1998 | Caspers | 623/34 |

(Continued)

FOREIGN PATENT DOCUMENTS

| | | | | |
|---|---|---|---|---|
| WO | WO91/01700 | * | 2/1991 | |
| WO | WO9919006 | * | 4/1999 | A61L/31/00 |

*Primary Examiner*—Alvin J. Stewart
(74) *Attorney, Agent, or Firm*—Bacon & Thomas, PLLC

(57) ABSTRACT

A volume control pad is provided for use in the socket of an artificial limb. The volume control pad has a core surrounded by a flexible shell. The core includes super absorbent polymer particles which form a gel upon the addition of water thereto. The volume control pad includes a tube for the introduction of water into the core portion of the pad. The volume control pad provides a simple and inexpensive means for adjusting the conformance of the socket around the residual limb from an initial swollen condition to a further point in time in which the swelling has diminished.

10 Claims, 6 Drawing Sheets

U.S. PATENT DOCUMENTS

| | | | | |
|---|---|---|---|---|
| 5,763,067 A | * | 6/1998 | Bruggemann et al. | 428/317.9 |
| 5,888,231 A | | 3/1999 | Sandvig | 623/36 |
| 5,904,722 A | | 5/1999 | Caspers | 623/34 |
| 5,930,949 A | | 8/1999 | Tsujimoto | 47/57.6 |
| 5,972,036 A | | 10/1999 | Kristinsson | 623/33 |
| 5,980,576 A | | 11/1999 | Graf | 623/33 |
| 6,033,769 A | * | 3/2000 | Brueggemann et al. | 428/305.5 |
| 6,037,094 A | | 3/2000 | Katampe | 430/138 |
| 6,068,620 A | | 5/2000 | Chmielewski | 604/378 |
| 6,117,176 A | | 9/2000 | Chen | |
| 6,123,694 A | | 9/2000 | Pieniak | 604/385 |
| 6,124,391 A | | 9/2000 | Sun | 524/447 |
| 6,149,691 A | | 11/2000 | Fay | 623/37 |
| 6,231,616 B1 | | 5/2001 | Helmy | 623/34 |
| 6,319,599 B1 | * | 11/2001 | Buckley | 428/308.4 |
| 6,368,357 B1 | | 4/2002 | Schon et al. | 623/37 |
| 2004/0232068 A1 | * | 11/2004 | Johnston et al. | 210/502.1 |

* cited by examiner

ARTIFICIAL LIMB SOCKET CONTAINING VOLUME CONTROL PAD

This application claims the benefit of Provisional application Ser. No. 60/237,381, filed Oct. 4, 2000.

BACKGROUND OF THE INVENTION

1. Field of the Invention

The present invention pertains to the field of artificial limbs for use by individuals who have lost a limb, especially a foot, through injury or amputation. More particularly the invention is directed toward an improved socket of an artificial limb into which the residual limb or amputation stump is mounted.

2. Background Information

Artificial limbs typically include a socket which is used to support and connect the residual limb of a patient to the artificial limb. The residual limb is inserted into the socket and it is therefore desirable that the socket should have a close fit around the residual limb to provide a good connection between the residual limb and the artificial limb with a minimum amount of pressure points on the residual limb. For this reason the sockets are custom made so that they conform to the configuration of the residual limb so as to be capable of supporting weight, in the case of a leg, or loading forces, in the case of an arm.

It has been found that it is highly desirable for patients to begin use of artificial limbs or prosthetic devices as soon as possible after loss of the limb through accident or amputation. If a patient can be fitted with a prosthetic device after limb amputation, the prognosis for long term, effective use of the prosthetic device is much higher. However, it is very difficult to obtain a good fit around the residual limb soon after loss of the limb through amputation or accident. This is because of the substantial edema or swelling which takes place after the loss of the limb regardless of whether the loss of limb is caused by amputation or injury. The edema will continue for about two or three months until sufficient healing has taken place which allows the fluids to be reabsorbed from the area of swelling.

Since limb prosthetic devices are most typically mounted to a patient by a socket which is customized to the configuration of the patient's residual limb, formation of a prosthetic socket within a few weeks of limb amputation results in a socket which conforms to the configuration of the swollen or edema-affected residual limb. However, as the edema or swelling gradually diminishes, the initial close fit will become more loose.

One approach for dealing with the gradual loosening of the fit between the residual limb and the socket has been the addition of increasing layers of socks over the residual limb before placing the residual limb in the socket. The additional socks are used to fill the space left in the socket as a result of decreasing edema.

Another approach is to simply recast the socket after the edema has disappeared. This approach is obviously costly. Still another approach is to wait until the edema has subsided before forming the prosthetic socket. This approach, however, is undesirable because it does not permit the amputee to obtain the therapeutic benefits associated with early use of the prosthetic device.

The above-noted use of socks is also undesirable because the socks change in volume with pressure, which means that the fit of the socket is dependent on the loads applied, hence the actions of the user. Another problem with such socks is loss of control, as multiple plies of socks allow the socket to rotate and move on the residual limb.

Several attempts have been made to manufacture a device that allows the user to control the volume of the socket. These include air bladders and various types of pumping mechanisms. These devices function on a pneumatic principle wherein air is used as a media to change the volume. The main problem with using air is that it is compressible and therefore the same problems occur as with the socks.

SUMMARY OF THE INVENTION

Accordingly, it is an objective of the present invention to provide an artificial limb having a socket which provides better conformance to the patient's residual limb.

It is also an objective of the present invention to provide the socket of an artificial limb with a simple and inexpensive means for adjusting the conformance of the socket around the residual limb from an initial swollen condition to a further point in time in which the swelling has diminished.

A further objective of the present invention is to provide an apparatus which minimizes pain and discomfort to the patient and which can be used with patients who have substantial residual limb swelling or edema.

These and other objectives are achieved by providing a volume control pad which contains a water permeable porous flexible matrix, such as open-cell foam, having conventional super absorbent polymeric particles in the pores or open spaces thereof (i.e., open cells in the case of open-cell foam). Super absorbent polymer is known in the trade as SAP. The water permeable porous flexible matrix containing the SAP is surrounded or protected by a waterproof flexible liner or shell. For example, the water permeable porous compressible matrix containing the SAP particles may be contained in a waterproof pouch, envelope or the like or may be confined between waterproof layers which form part of the socket. It is also possible to practice this invention without the SAP being contained in the open spaces or pores of a water permeable porous flexible matrix. For example the SAP may simply be contained within the waterproof pouch, envelope or the like without any porous matrix material being present therein. Similarly the SAP may be contained between the waterproof layers which form part of the socket without any porous matrix material being present between these layers.

The volume control pad also includes means for introducing water therein for contact with the SAP particles so that the particles rapidly absorb the water to thereby form a gel in accordance with known principles. The formation of the gel greatly expands the volume of the SAP material with the amount of volume increase depending on the amount of added water.

The volume control pad includes means for the user to periodically add water for adjusting the volume of the pad. A flexible tube is conveniently used for the addition of water. One end of the tube is connected to the pad so that water passing through the tube enters the core portion of the pad which contains the SAP particles (i.e., in fluid connection with the pad). The other end of the tube may include any conventional valve mechanism which can be opened and closed to allow the introduction of water when the valve is opened and to prevent evaporation afterwards when the valve is closed. The terminal portion of the tube may also include an adapter which facilitates connection of a fluid injection means such as a syringe or other type of manually activated pump.

The volume control pad is advantageously placed in any desired location in the socket. Typically the pad will be used in the same location that conventional pressure relief formations are currently used in prosthetic sockets.

The SAP particles distributed in the open cell sponge or within the pores or open spaces of other types of water permeable porous flexible materials, allow the gel to have highly desirable physical characteristics. In particular, the gel, being composed of water and solid polymer, is noncompressible like nongelled water. In addition the gel within the foam or other water permeable porous flexible material behaves like a solid and is sufficiently flexible or compliant so that the pad conforms to the shape of an object against which it is in contact without development of high pressure points. Thus the gel will conform to the shape of the socket located on one side and the sleeve of the residual limb on the other side.

In contrast, gas filled pads are undesirable because of the compressible nature of the gas. Also, although water is noncompressible, the use of nongelled liquids is undesirable because nongelled liquids when introduced into a flexible container do not behave like a solid.

DETAILED DESCRIPTION OF THE INVENTION AND PREFERRED EMBODIMENTS

Figures 1, 2:
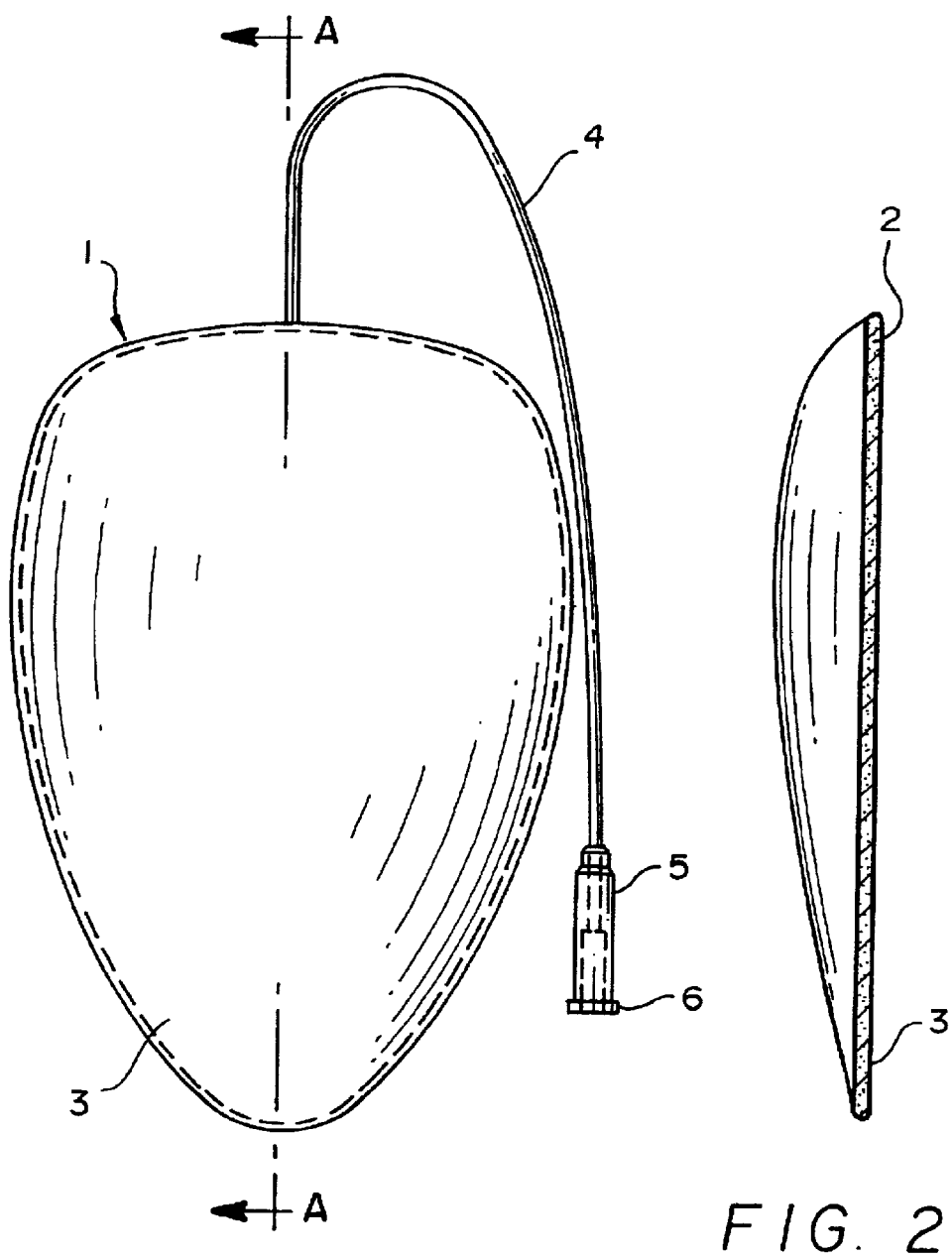
FIG. 1 illustrates a preferred embodiment of the volume control pad of the invention.
FIG. 2 is a cross-sectional view of the control pad of the invention taken along line A—A of FIG. 1.

In a preferred embodiment the SAP particles are incorporated within the cells of an open-cell polymeric foam. The particles may be incorporated into the open cells of the foam during the polymeric foam forming process according to known techniques. Any polymeric material capable of forming open-cell foam according to known procedures may be used in this invention. A preferred foam is silicone foam.

Super absorbent polymer or SAP is a well known class of polymeric material which absorbs a large amount of water (e.g., 20 times the weight of the polymer) to form a viscous gel material. Such materials are well known to those skilled in the art.

Super absorbent polymer is generally a water-insoluble but water-swellable polymeric substance capable of absorbing water in an amount which is at least 10 times the weight of the substance in its dry form. In one type of super absorbent material, the material is described chemically as having a backbone of natural or synthetic polymers with hydrophilic groups or polymers containing hydrophilic groups being chemically bonded to the backbone or an intimate admixture therewith. Included in this class of materials are such modified polymers as sodium neutralized cross-linked polyacrylates and polysaccharides including, for example, cellulose and starch and regenerated cellulose which are modified to be carboxylated, phosphonoalkylated, sulphoxylated or phosphorylated, causing the SAP to be highly hydrophilic. Such modified polymers may also be cross-linked to reduce their water solubility.

Super absorbent polymers are known to those skilled in the art as a chemical product having an insolubilized structure as derived by a suitable method from a water-soluble polymer such as polyelectrolyte and includes, for example, cross-lined polyacrylic acid salts, cross-lined isobutylene-maleic acid copolymer derivatives, cross-linked starch-polyacrylic acid salts, cross-linked polyvinyl alcohol-polyacrylic acid salts, cross-linked polyvinyl alcohol derivatives, cross-linked polyethylene glycol derivatives and cross-linked carboxymethylcellulose derivatives.

Super absorbent polymers are made by conventional methods such as the methods described in the journal article "Keeping dry with superabsorbent polymers", Chemtech, (September 1994) by Buchholz.

Additional examples of super absorbent polymers which are known in the art include vinyl alcohol polymers or copolymers; acrylic or methacrylic acid polymers or copolymers; sodium or potassium salts of acrylic or methacrylic acid polymers or copolymers; and alkyl, hydroxylalkyl, or hydroxylalkyl ether esters of acrylic or methacrylic acid polymers or copolymers. Examples of commercially available super absorbent polymers include Sigma-Aldrich Cat. No. 41602-9 (polyacrylic acid sodium salt); Sigma-Aldrich Cat. No. 43532-5 (polyacrylic acid potassium salt); Nippon Shokubai K.K., AQUALIC AS-58 (polyacrylic acid); Nippon Shokubai K.K., AQUALIC CA (type ML-10) (cross-linked acrylic acid-sodium acrylate copolymer); Nihon Jonyaku Co., Ltd., JURYMER AC-10L (polyacrylic acid); Nihon Jonyaku Co., Ltd., JURYMER AC-105 (polyacrylic acid); Arakowa Chemical Industries, Ltd., ARASORB-F; and Sumitomo Seika Chemicals Co., Ltd., AQUAKEEP-10SH-NF.

Further well known SAP materials are described in U.S. Pat. No. 5,409,771, the specification of which is incorporated herein.

A preferred super absorbent polymer is a salt (e.g., sodium or potassium) of cross-linked polyacrylic acid/polyalcohol grafted copolymer. This preferred polymer is commercially available as FAVOR® SAB 800 from Stockhausen Inc. located at 2401 Doyle St., Greensboro, N.C. 27406. The FAVOR® SAB 800 super absorbent polymer has the following characteristics:

Chemical basis: salt of cross-linked polyacrylic acid/polyalcohol grafted copolymer Physical form: white granules Particle size: 100–850 microns Product density: 540 g/l +/–30

Sifting properties: free flowing

Moisture content: 5% +/–2 pH value (1% gel @ 0.9% NaCl): 6.0+/–0.5

Storage: more than one year under dry conditions

The carboxylic groups of the FAVOR® SAB 800 super absorbent polymer are solvated when brought into contact with water or water based liquid. As a result, the groups partially dissociate into negatively charged carboxylic ions. In this state the polymer chain contains a large number of similarly charged ionic groups which repel each other. The polymer coils become more bulky and thus extend their propensity to absorb increasing quantities of the aqueous liquid. This process would normally lead to a complete solution of the polymer. However, due to the cross-linking between the polymer chains of FAVOR® SAB 800 super absorbent polymer, only the formation of a gel takes place, preventing its solution. The water is strongly bonded by means of hydrogen bonds in the gel.

Preferred foams are open-cell foams having densities from 20 to 500 kg/m$^3$ with preferred densities being in the range from 100 to 200 kg/m$^3$. In a preferred embodiment the foam is prepared from silicone rubber such as elastomeric silicone. The SAP is incorporated into the foamed silicone by mixing the particles of SAP with the uncured silicone prior to foaming and curing. Thus, silicone containing an appropriate foaming and curing agent is mixed with the SAP particles and then subjected to foaming and curing conditions to produce an open celled foam.

The foam containing the SAP particles therein constitutes the core section of the volume control pad. The core is enclosed within a flexible shell or envelope. It is thus possible to make a volume control pad without resorting to the use of the foam. In particular, a volume control pad can be made without foam by bridging opposing portions of the flexible outer shell at several locations to thereby form an open cell structure within the flexible shell. In addition the SAP may simply be incorporated within a waterproof flexible liner or shell without the creation of a plurality of open cells therein (i.e., there being only one open space in the flexible liner or shell to contain the SAP therein).

The invention will now be more particularly described by reference to the accompanying figures.

Figure 3:
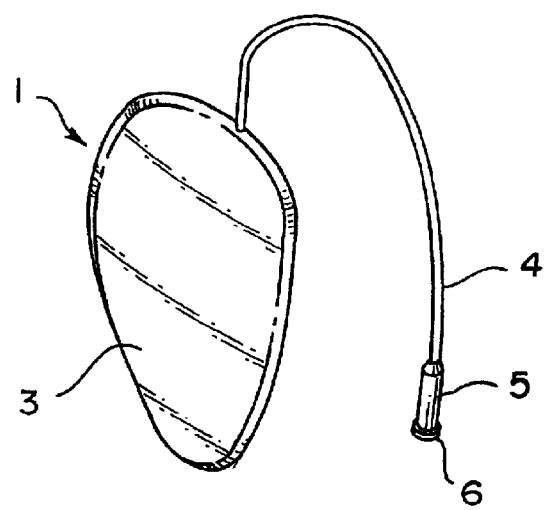
FIG. 3 is an isometric view of the volume control pad of the invention.

FIGS. 1–3 show a preferred embodiment of the volume control pad used in the present invention. The volume control pad, shown generally by reference numeral 1, includes a core 2 encased or enveloped within a flexible shell 3 which is preferably made of silicone with textile reinforcement. A core 2 of open-cell silicone foam containing SAP particles within the cells thereof is located within flexible shell 3. According to one embodiment of the invention the core may simply comprise a volume of space (i.e., core volume space) within the flexible liner or shell for containing the SAP material without the presence of the open celled foam. A flexible silicone tube, which is attached to the pad, is in fluid communication with the core 2 for the introduction of water into the core so that a gel is formed within the shell. Preferably the tube is attached to the top portion of the pad so that air within the core that is displaced by the addition of water, can easily be vented and removed.

Flexible tube 4 is made of conventional medical or surgical tubing such as silicone tubing. The flexible tube 4 terminates with an adapter or coupling device which may be used for temporarily connecting the tube to a source of water (e.g., water containing syringe or the like). The adapter or coupling 5 includes a cap 6 which is removed when water is introduced into the pad and replaced to prevent unwanted evaporation.

Figures 9, 10:
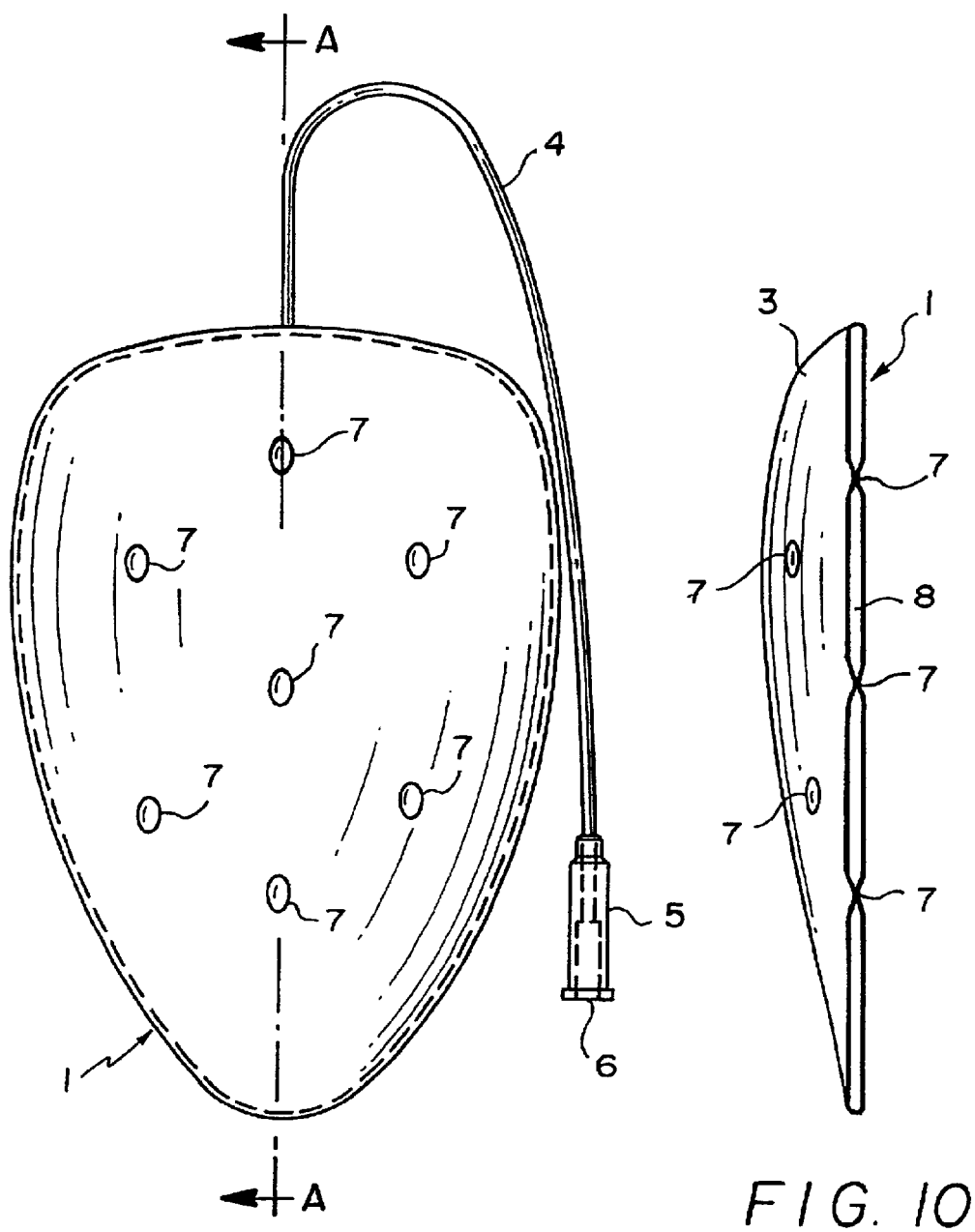
FIG. 9 illustrates an alternative embodiment of the core portion of the volume control pad in which the open spaces for containing the SAP particles are formed by bridging portions of the flexible shell.
FIG. 10 is a perspective cross-sectional view of FIG. 9 along line A—A.

FIGS. 9 and 10 illustrate an alternative embodiment of the pad which lacks the open cell foam. Instead of open cells provided by the foam for holding the SAP particles, the embodiment shown in FIGS. 9 and 10 provide a large open cell volume by bridging or sealing opposite sides of the flexible shell together at a plurality of locations. For example, the two sides of the shell can be fused together at a plurality of locations 7 shown in FIGS. 9 and 10 to thereby convert the inner volume of the flexible shell into a large open cell structure 8. The aforementioned bridging or sealing of the opposite sides of the shell may be omitted to thereby provide an uninterrupted volume within the shell to contain SAP particles therein.

The volume control pad is advantageously incorporated within the socket which is used to receive and hold the terminal portion of a residual limb of an individual from whom a portion of the limb has been severed due to amputation or injury. Such sockets such as the sockets described in U.S. Pat. No. 5,972,036 are well known to those skilled in the art. The sockets to which the present invention is used generally have an opening at one end for receiving the residual limb and a cup shaped interior which is shaped to receive the residual limb of an amputee. Typically the cup shaped interior is shaped to conform to the shape of the residual limb which is to be inserted therein. In particular the shaped socket is sized to conform to the shape of the residual limb upon which a sleeve, stocking pad, comfort liner or the like is worn. Such sleeves, comfort liners or stocking pads are well known and are shaped of resilient material for conformation with the shape of the residual limb.

Figure 4:
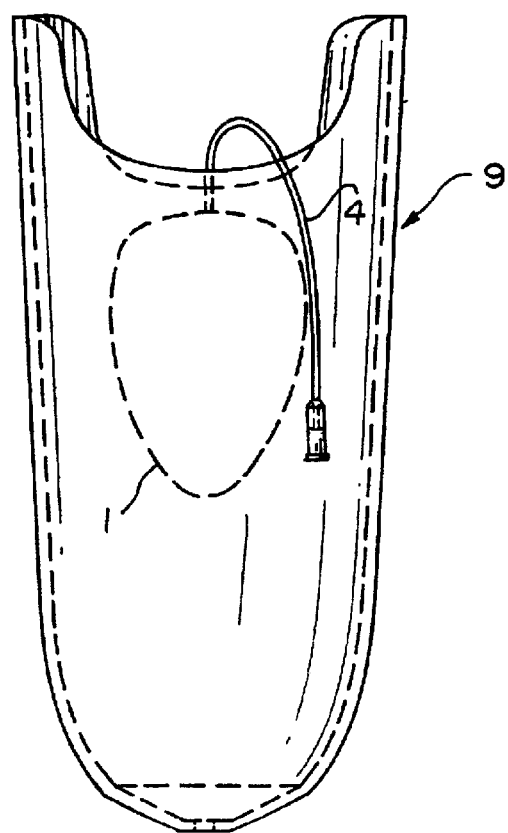
FIGS. 4–6 illustrate a prosthetic socket which contains a volume control pad in accordance with the present invention.
Figures 5, 6:
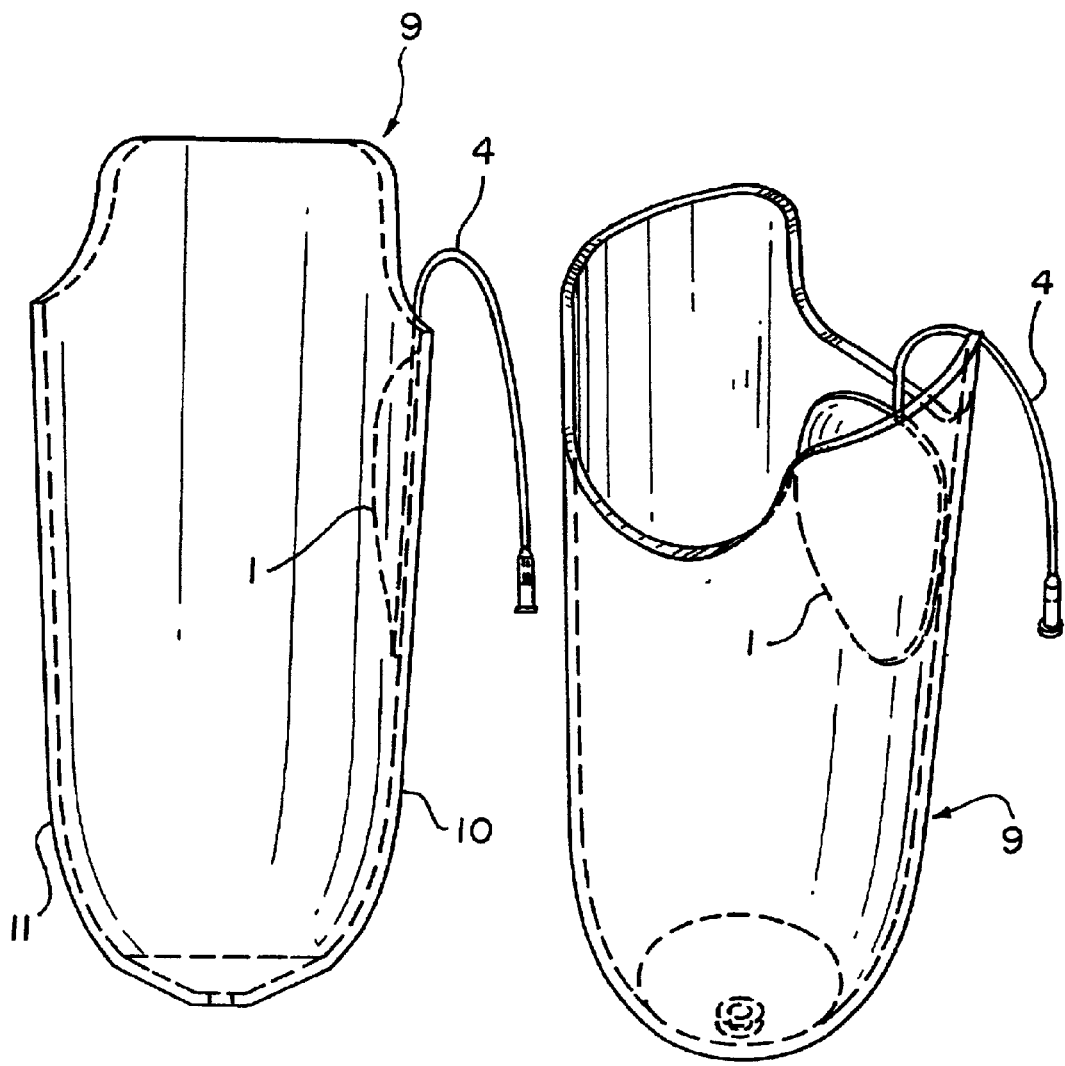

FIGS. 4–6 illustrate a conventional socket within which the volume control pad is used in accordance with this invention. As shown in FIG. 4, the control pad 1 is mounted or adhered within the socket 9 at any desirable location. For example an appropriate position for the control pad corresponds to the positions for pressure relief formations used in the socket described in U.S. Pat. No. 5,972,036, the disclosure of which is incorporated herein by reference. The skilled prosthetist will understand how and where such pressure relief formations must be provided in accordance with known techniques so that they can provide pressure relief for sensitive areas of the residual limb during use. The volume control pad may be incorporated within the socket in accordance with the procedure described in U.S. Pat. No. 5,972,036 for the incorporation of pressure relief formations in the socket.

FIGS. 4, 5 and 6 are different views of the same socket which contains volume control pad 1 mounted therein. As shown in FIG. 5, the socket has a posterior side 10 and an anterior side 11. The volume control pad in FIGS. 4, 5 and 6 is mounted on the posterior side 10. The tube 4 is positioned so that the user can introduce water into the pad when the residual limb is contained in the socket. For example, the tube may be molded in the material which forms the socket with a portion extending therefrom on the outside for access by the user.

Figure 7:
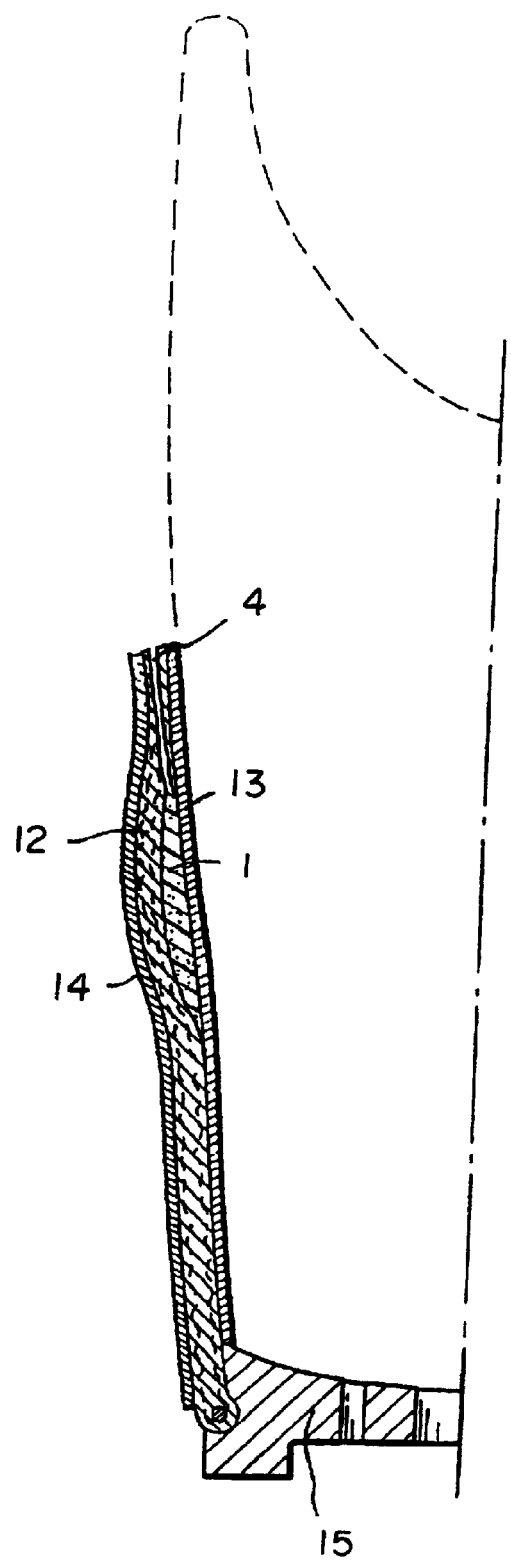
FIG. 7 illustrates a cross-section portion of a socket showing the location of a volume control pad in a prosthetic socket according to an embodiment of the invention.

FIG. 7 illustrates an embodiment of the invention wherein the volume control pad replaces the pressure relief formations described in U.S. Pat. No. 5,972,036. More particularly, FIG. 7 illustrates a cross-section of a portion of a socket such as the type of socket described in U.S. Pat. No. 5,972,036 in which the pressure relief formation is replaced by the volume control pad of the present invention. As shown in FIG. 7, the volume control pad 1 is incorporated in the socket between wall material 12 and a smooth fabric inner liner layer 13. The embodiment illustrated in FIG. 7 can be made according to the technique described by U.S. Pat. No. 5,972,036 by substituting the volume control pad of the present invention with the pressure relief formation used in the aforementioned patent. Thus the socket illustrated in FIG. 7 corresponds to the socket described in U.S. Pat. No. 5,972,036 with the exception being the replacement of the pressure relief formation with the volume control pad of the present invention. Accordingly FIG. 7 also illustrates the inclusion of a smooth fabric outer covering layer 14 and a coupler 15.

Figure 8:
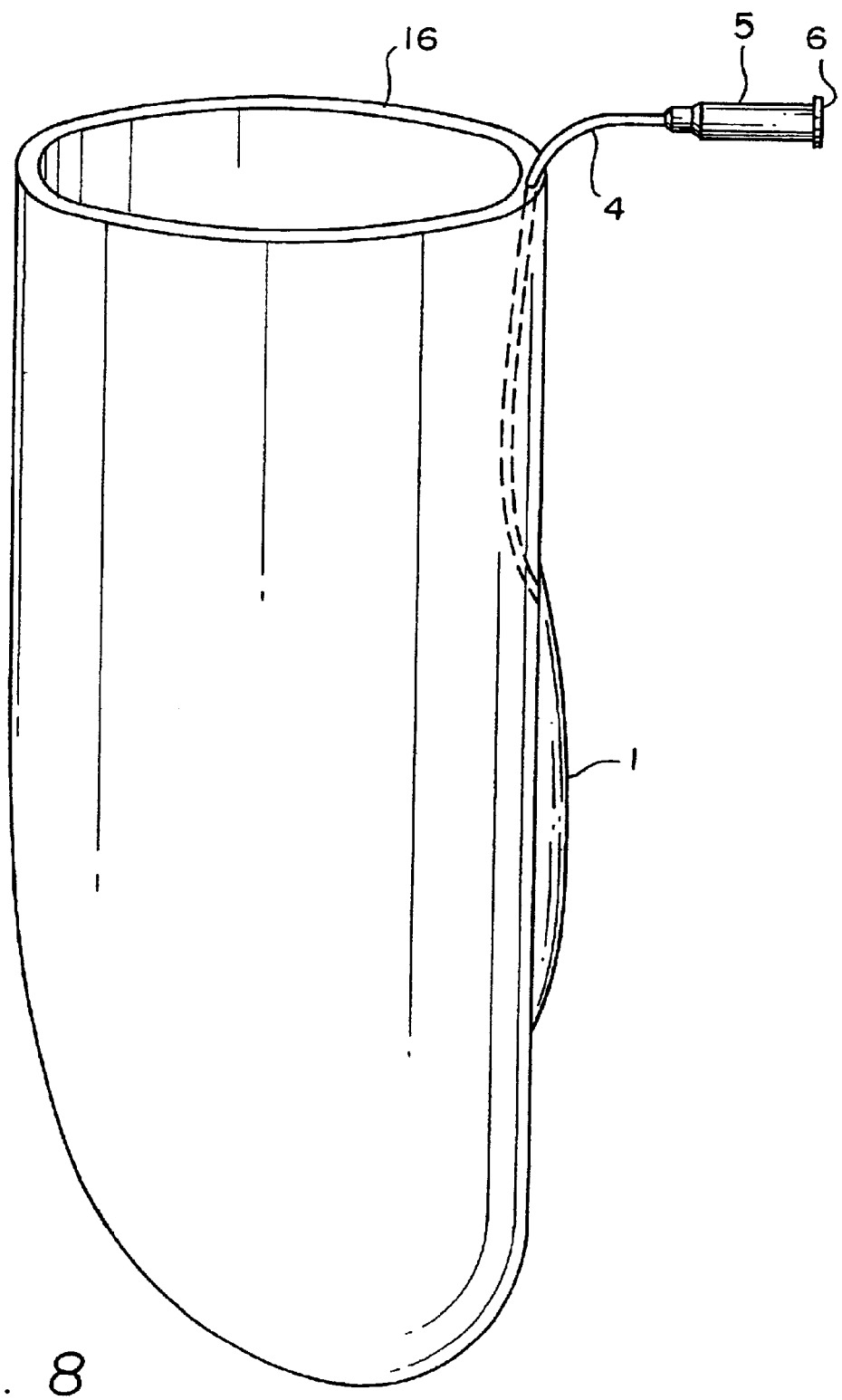
FIG. 8 illustrates an embodiment of the invention wherein the volume control pad is bonded to the sleeve or similar structure worn over the residual limb.

In an alternative embodiment the volume control pad is mounted on the sleeve, comfort liner or stocking pad which the amputee wears on the residual limb. In this embodiment the volume control pad is mounted on the outside surface of the sleeve, stocking pad, comfort liner or the like so that the adjustable comfort pad is situated between the sleeve, stocking pad, comfort liner or the like and the socket. This embodiment of the invention is illustrated in FIG. 8. As shown in FIG. 8 volume control pad 1 is secured (for example by adhesive) to sleeve 16.

The silicone polymer used in the present invention may be any of the well known silicone rubber or elastomer materials which are readily available. Preferably the silicone should be medical grade or silicone suitable for use in medical applications.

While the present invention has been described in terms of certain preferred embodiments, one skilled in the art will readily appreciate that various modifications, changes, omissions, and substitutions may be made without departing from the spirit thereof. It is intended, therefore, that the present invention be limited solely by the scope of the following claims.

What is claimed is:

1. A volume control pad for use in a socket of an artificial limb; said volume control pad comprising a core contained in a fluid-impermeable flexible shell; a tube attached to said flexible shell in fluid communication with said core for the introduction of fluid into said core; said core comprising an open-cell foam having open cells containing particles of super absorbent polymer therein.

2. The volume control pad of claim 1 wherein said flexible shell, said tube or said open-cell foam is silicone.

3. The volume control pad of claim 2 wherein said tube has a terminal end remote from said flexible shell and said terminal end of the tube having an adapter for connection with a fluid source; said adapter having a cap located thereon to prevent evaporation of fluid through said tube, said cap being removable to allow the introduction of fluid into said tube.

4. The volume control pad of claim 3 wherein said super absorbent polymer comprises the salt of cross-linked polyacrylic acid/polyalcohol grafted copolymer.

5. In a socket for an artificial limb, said socket having a residual limb receiving opening at one end and a cup shaped interior which is shaped to receive the residual limb of an amputee; wherein the improvement comprises the volume control pad of claim 1 mounted in the cup shaped interior of said socket.

6. A method for adjusting the conformance of a socket of an artificial limb around a patient's residual limb inserted within said socket, said process comprising:

providing a volume control pad within said socket, said volume control pad comprising a core within a flexible shell with super absorbent polymer contained within said core;

causing said super absorbent polymer to swell by introducing fluid within said core containing said super absorbent polymer so that said super absorbent polymer absorbs the fluid.

7. The method of claim 6 wherein said volume control pad is provided within said socket by being mounted within said socket.

8. The method of claim 6 wherein said socket includes a wall and a fabric inner liner on said wall and said volume control pad is provided between said fabric inner liner and said wall.

9. The method of claim 6 wherein said volume control pad is provided within said socket by mounting said volume control pad on a sleeve, liner or stocking pad worn on said residual limb.

10. The method of claim 6 wherein said shell comprises fluid impermeable layers which form part of said socket.

* * * * *